United States Patent
Tang et al.

(10) Patent No.: US 12,083,166 B2
(45) Date of Patent: Sep. 10, 2024

(54) PHARMACEUTICAL COMPOSITION INCLUDING LAMININ FRAGMENTS TO TREAT OR PREVENT THE DISEASE, DISORDER OR SYMPTOM OF TOOTH DENTIN AND/OR DENTAL PULP

(71) Applicant: Takashi Saito, Ebetsu (JP)

(72) Inventors: Jia Tang, Sapporo (JP); Takashi Saito, Ebetsu (JP)

( * ) Notice: Subject to any disclaimer, the term of this patent is extended or adjusted under 35 U.S.C. 154(b) by 0 days.

(21) Appl. No.: 18/057,110

(22) Filed: Nov. 18, 2022

(65) Prior Publication Data

US 2023/0190882 A1 Jun. 22, 2023

Related U.S. Application Data

(62) Division of application No. 16/825,116, filed on Mar. 20, 2020, now abandoned.

(60) Provisional application No. 62/821,023, filed on Mar. 20, 2019.

(51) Int. Cl.
*A61K 38/39* (2006.01)
*A61K 33/42* (2006.01)
*A61K 38/01* (2006.01)

(52) U.S. Cl.
CPC .............. *A61K 38/39* (2013.01); *A61K 33/42* (2013.01); *A61K 38/014* (2013.01)

(58) Field of Classification Search
None
See application file for complete search history.

(56) References Cited

PUBLICATIONS

Oyane et al, "Calcium phosphate composite layers for surface mediated gene transfer." Acta Biomaterialia (2013) 8 p. 2034-2046.*

Fujiwara, Hironubu et al; "Purification and characterization of human laminin 8" J. Biol. Chem. (2001) 276(18) p. 17550-17558.*

Sasaki, Rie et al; "Fabrication and evaluation of multiple pdna-hydrozyapatite particles for transfection to hek293 cells." J. Unexplored Med. Data. (2018) 3(6).*

Hao, Jianjun et al; "Odontoblast cells immortalized by telmoerase produce mineralized dentin like tissue both in vitro and in vivo." J. Biol. Chem. (2002) 277(22) p. 19976-19981.*

Domogatskaya, Ann et al; "Laminin-511 but not -322, -111, or -411 enables mouse embryonic stem cell self renewal in vitro." Stem Cells (2008) 26 p. 2800-2809.

Nagai, Akiko et al; "Mouse embryonic stem cultured under serum and feeder free conditions maintain their self renewal capacity on hydroxyapatite, "Mat. Sci. Engin. C (2014) 34 p. 214-220.

* cited by examiner

*Primary Examiner* — Fred H Reynolds
(74) *Attorney, Agent, or Firm* — WHDA, LLP

(57) ABSTRACT

A tooth dentin, pulp or pulp tissue composition for treating or preventing a disease, disorder, or symptom of a tooth dentin and/or pulp or pulp tissue includes: (a) an integrin binding fragment of Laminin, the Laminin being selected from the group consisting of Laminin 511 and Laminin 411, the integrin binding fragment comprising an integrin-binding domain of the Laminin; and (b) a mixture of odontoblast and mineralized nodules secreted from the odontoblast. A coating density of the integrin binding fragment is 1 to 8 $\mu g/cm^2$. The material (b) has been mixed with the material (a) in the composition so as to form pulp capping applicable to a tooth, such that the composition is able to treat or prevent the disease, disorder or symptom of the tooth dentin and/or pulp tissue including dental caries when applied to the tooth.

1 Claim, 14 Drawing Sheets

Specification includes a Sequence Listing.

PHARMACEUTICAL COMPOSITION INCLUDING LAMININ FRAGMENTS TO TREAT OR PREVENT THE DISEASE, DISORDER OR SYMPTOM OF TOOTH DENTIN AND/OR DENTAL PULP

CROSS-REFERENCE OF RELATED APPLICATION

This application is a divisional application of U.S. application Ser. No. 16/825,116 filed Mar. 20, 2020, which claims priority to Provisional Application No. 62/821,023 file Mar. 20, 2019, the entire contents of which are incorporated herein by reference.

TECHNOLOGY FIELD

This invention relates to a pharmaceutical composition, drug or medicine including laminin fragments to treat or prevent the disease, disorder or symptom of tooth dentin and/or dental pulp. It also relates to a method for the preparation of the hard tissue transplant materials for the tooth by culturing odontoblasts in the presence of laminin fragments. Moreover, it relates to a prevention method of caries occurrence on the surface of the tooth.

The sequence listing submitted in a computer readable form under the name of "P190307US02_SEQLIST_2-1-2023.xml" is hereby incorporated by reference into the present application. The electronic copy of the sequence listing in the computer readable form, the file size of which is 29K bytes, was created on Feb. 1, 2023.

BACKGROUND TECHNOLOGY

The pulp which was exposed with being untreated causes serious infection by deep caries in the pulp tissue and tooth root-surrounding tissue. The infection of the pulp tissue and tooth root-surrounding tissue causes the loss of teeth as a worst possible outcome, and not only it adversely affects oral aestheticity, but also this reduces quality of life remarkably. Calcium hydroxide is generally used to perform capping of exposed pulp, and to cure. However, there is a fault to be easy to cause inflammation because calcium hydroxide is high alkaline. The success rate for nine years of the treatment using calcium hydroxide is reported as 58.7% (non-patent document 1), and enough clinical effectiveness is not provided.

Because possibility of the pulpal infection increases when pulp tissue is exposed for a long term, it is necessary to carry out invasive treatment, it is called, root canal treatment. Complications might occur by the root canal treatment, and ability for tooth sense and tooth formation is lost more. Therefore, it is extremely important to block up the caries portion before infection arrives at the pulp tissue and maintain dentin structure. The odontoblasts existing at the outer stratum of the pulp tissue secretes dentin substrate and can continue making dentin. Therefore, the development of drug and transplant materials to promote dentin formation (regeneration) used to prevent the exposure of the pulp tissue and cure it. For example, patent document 1 lists dentin regenerating materials including at least one kind of the synthetic peptide including the RGD sequence of phosphophoryn which maintained hard tissue inducing activity. Patent document 2 lists a drug containing effective protein having matrix metalloprotease 3 activity as an active ingredient for regenerating activity for pulp tissue and dentin. Patent document 3 lists the dentin regenerating accelerant which assumes an HMG-CoA reductase inhibitor as an active ingredient.

Laminin (LN) is a heterotrimeric glycoprotein including α, β and γ chain. The glossology of LN is based on the chain composition, e.g., LN-411 (alias LN-8) includes α 4, beta 1 and γ 1 chain, and LN-511 (alias LN-10) includes α 5, beta 1 and γ 1 chain. Laminin is an important component of the basement membrane and regulates extended cell activity such as a proliferation (non-patent document 2), migration (non-patent document 3 and 4), the differentiation (non-patent document 5 and 6). Laminin is fragmented in seven domains namely E3, T8, E8, C8-9, C1-4, P1 and E4 by proteolysis (non-patent document 7).

iMatrix-411 which is the high-purity refined production of the E8 fragment derived from LN-411 maintains complete binding activity for integrin, but lacks in the binding activity to other cell matrix components (non-patent document 8). It is reported that iMatrix-411 induces the differentiation from the human iPS cells into the cholangiocytes by upregulating some cholangiocyte markers such as aquaporin 1, SRY-box9 (SOX9), Jagged 1 (JAG1) and the secretin receptor (SCTR) (non-patent document 9).

It is reported that LN-511 is intensive adhesive of the cell in the epithelial cell origin (non-patent document 10). iMatrix-511 which is the high-purity refined production of the E8 fragment derived from LN-511 has integrin binding activity, and more intensive adhesive property for a human embryonic stem cell and human inductivity pluripotent stem cells (hiPSC) than intact LN-511 (non-patent document 11). In addition, the pre-coating method is generally used for the usage of iMatrix-511 and iMatrix-411, but it is reported about iMatrix-511 that a method to add in a cell suspension directly promotes a cell adhesion effect in a more low-concentrated laminin fragment effectively, than the pre-coating method (patent document 5).

As medical care materials containing a laminin, treatment drug or prevention drug including at least one factor chosen among the group consisting of laminin and the laminin fragments, including γ 1 chain is listed in patent document 4, for the disease, disorder or symptom of the retina pigment epithelium.

BACKGROUND ART DOCUMENTS

[patent document 1] Japanese Patent Laid-Open No. 2009-286767 bulletin
[patent document 2] Japanese Patent Laid-Open No. 2009-249344 bulletin
[patent document 3] WO2008/120720
[patent document 4] WO2016/067629
[patent document 5] Japanese Patent Laid-Open No. 2017-85963 bulletin

Non-Patent Document

[Non-patent document 1] Willershausen B, Willershausen I, Ross A, Velikonja S, Kasaj A, Blettner M. It is 165-71, 2011 Quintessence Int 42.
[non-patent document 2] Dowgiert J, Sosne G, Kurpakus-Wheater M. It is 161-75, 2004 Cell Prolif 37.
[Non-patent document 3] Desban N, Duband J L. J Cell Sci 110 (Pt 21): 2729-44, 1997.
[Non-patent document 4] Suh H N, Han H J. Laminin regulates mouse embryonic stem cell migration: involvement of Epac1/Rap1 and Rac1/cdc42. It is C1159-69, 2010 298.

[Non-patent document 5] Albini A, Noonan D M, Melchiori A, Fassina G F, Percario M et al. It is 2257-2261, 1992 Proc Natl Acad Sci USA 89.

[Non-patent document 6] Turck N, Lefebvre O, Gross I, Gendry P, Kedinger M et al. It is 545-555, 2006 J Cell Phy 206.

[Non-patent document 7] Beck K, Hunter I, Engel J. It is 148-160, 1990 The FASEB Journal 4.

[Non-patent document 8] Ohta R, Niwa A, Taniguchi Y, Suzuki N M, Toga J, Yagi E et al. Scientific Reports 6:35680, 2016.

[Non-patent document 9] Takayama K, Mitani S, Nagamoto Y, Sakurai F, Tachibana M et al. It is 91-96, 2016 Biochemical and Biophysical Research Communications 474.

[non-patent document 10] Pouliot N, Saunders N A, Kaur P. It is 387-97 Exp Dermatol 2002, 11.

[Non-patent document 11] Miyazaki T, Futaki S, Suemori H, Taniguchi Y, Yamada M, Kawasaki M, et al. Nat Commun 2012, 3:1236.

SUMMARY OF THE INVENTION

As described above, a problem for the development of drug and transplant materials to promote dentin formation (regeneration) exists, but conventional drug to promote dentin formation, for example, induces odontoblast differentiation from pulpal stem cells and mesenchymal stem cell, and does not act in odontoblasts directly. Thus, the application of the conventional drug into dental treatment was restrictive. In addition, there is a report about the usage of a laminin fragment other than the use as the substrate for the cell culture, that it promotes the cell adhesion of retina pigment epithelium and/or the nerve. But the action to odontoblasts and the use for caries prevention in the dentistry field of the laminin fragment are not known.

The purpose of this invention is to provide a drug to promote dentin formation (regeneration) and a method to prepare hard tissue transplant materials from odontoblasts. In one aspect of the present invention, a tooth dentin, pulp or pulp tissue composition for treating or preventing a disease, disorder, or symptom of a tooth dentin and/or pulp or pulp tissue includes: (a) an integrin binding fragment of Laminin, the Laminin being selected from the group consisting of Laminin 511 and Laminin 411, the integrin binding fragment comprising an integrin-binding domain of the Laminin; and (b) a mixture of odontoblast and mineralized nodules secreted from the odontoblast. A coating density of the integrin binding fragment is 1 to 8 µg/cm². The material (b) has been mixed with the material (a) in the composition so as to form pulp capping applicable to a tooth, such that the composition is able to treat or prevent the disease, disorder or symptom of the tooth dentin and/or pulp tissue including dental caries when applied to the tooth.

According to this invention, the following invention is offered.

[1] It provides a treatment or medicine to prevent it for the disease, the obstacle or the symptom of the dentin of the tooth and/or pulp tissue, including the integrin binding fragment of the laminin chosen among the group consisting of Laminin 511 and Laminin 411.

[2] It provides a treatment or medicine to prevent it for the disease, the obstacle or the symptom of the dentin of the tooth and/or pulp tissue, including the integrin binding fragment of the laminin chosen among the group consisting of Laminin 511 and Laminin 411, and porous hydroxyapatite or type I collagen further. [3] The manufacturing method of the hard tissue transplant materials of the tooth including a process to culture odontoblast in the presence of the integrin binding fragment of the laminin chosen among the group consisting of Laminin 511 and Laminin 411, and to get a culture and the process to induce calcification for the above culture, and to get the hard tissue transplant materials of the tooth.

[4] The odontoblastic culture is a method of mention to [3] carried out at the culture dish surface coated an integrin binding fragment of the laminin chosen among the group consisting of Laminin 511 and Laminin 411.

[5] The coating density by the integrin binding fragment is a method of mention to [4] that is 1-8 µg/cm².

EMBODIMENTS OF THE INVENTION

Figure 1:
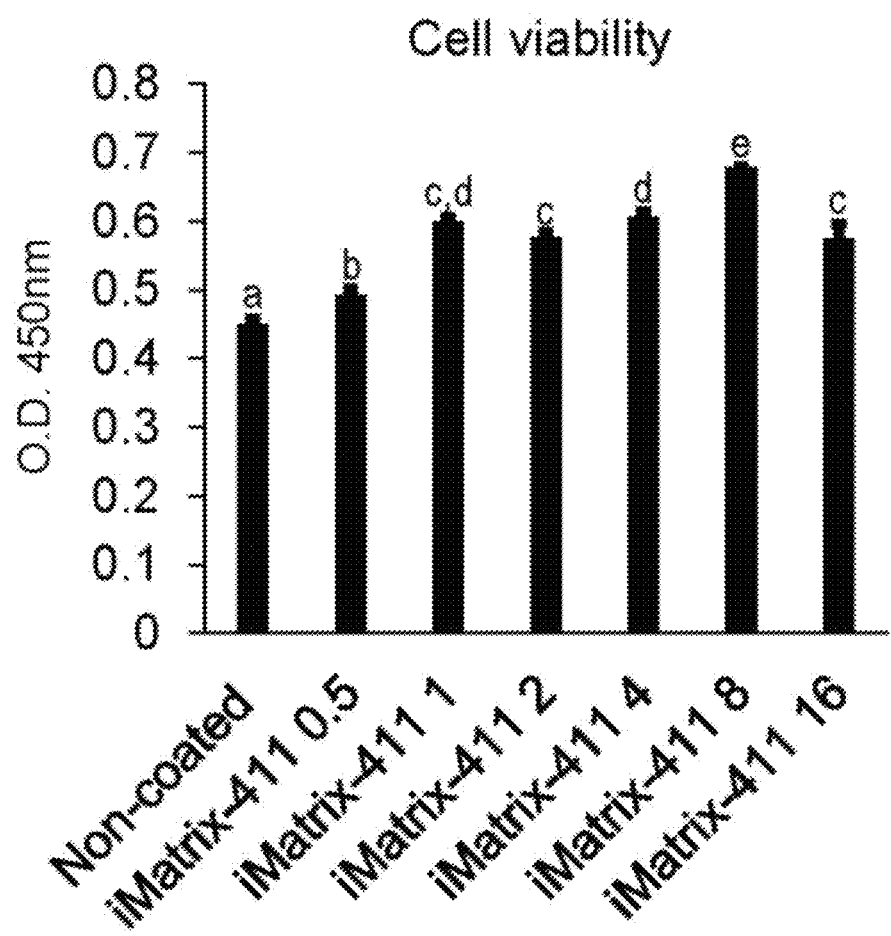
FIG. 1 The cell proliferation activity of the MDPC-23 cell in the different coating density of LN411-E8. The number (0.5, 1, 2, 4, 8, 16) following iMatrix-411 is coating density (µg/cm²) of N411-E8. Different letter a-e on the bar shows a significantly different thing in the meantime ($p<0.05$, post hoc Tukey HSD test).

The explanation of this invention to list below is not limited to a representative enforcement form and the enforcement form that it may be done based on a specific example, but this invention looks like it. In addition, the number range expressed using "-" in the instant specification means a range including a number listed in front and behind "-" as the lower limit level and the upper limit level.

[Composition for Treatment or Prevention for a Disease, Disorder or Symptom of the Dentin of the Tooth and/or Pulp Tissue]

This invention provides a pharmaceutical composition/medicine for treatment or prevention for a disease, disorder or symptom of the dentin of the tooth and/or pulp tissue including the integrin binding fragment of the laminin chosen among the group consisting of Laminin 511 and Laminin 411. The pharmaceutical composition/medicine of this invention is administered to dentin and a pulp tissue exposed by the damage and caries topically, and acts to odontoblast existing at the outer stratum of the pulp tissue to promote odontoblast proliferation and differentiation for dentin regeneration. The composition/medicine has a function to treat or prevent the disease, disorder or symptom of the tooth dentin and/or pulp tissue including dental caries. The composition/medicine can be in any form including mouse rinsing liquid.

The tooth consists of enamel, dentin, cement, pulps, and the dentin constitutes the hard tissue of the tooth with enamel and cement. The dentin is formed of the odontoblast which there is to the outer stratum of the pulp. The dentin formation refers to production and regenerating of dentin.

The laminin fragment to use for the process of the present invention is not limited in particular as long as it has an integrin binding property. The fact that the laminin fragment has an integrin binding property can be confirmed by a solid-phase combination assay. In this statement, an integrin binding laminin fragment is sometimes listed as a laminin fragment.

Laminin may be a nature type or modified modification types which maintains the biological activity and modified more than one amino acid residues. There is no limitation about origin and production method of laminin. Therefore, the laminin fragment used in this invention, can be naturally derived protein, protein produced using genetic technique or the chemical synthesis protein. A laminin fragment used in this invention can be a laminin fragment derived from *Homo sapiens* or a laminin fragment derived from a non-human animal. When used it for dental treatment of human, it is preferable to be a laminin fragment derived from *Homo sapiens*.

There is no limitation with regard to the property of laminin, be it naturally derived or decorated in more than one amino acid. Also, there is no limitation with regard to the origin or manufacturing method of laminin in this innovation. Therefore, the laminin fragment used in the current innovation may be derived naturally, or generated by genetic engineering technique. The laminin used in the current innovation may be from human or other animals. However, it would be preferable to use human derived laminin fragments in dental treatment.

Laminins are heterotrimeric proteins that contain an α-chain, a β-chain, and a γ-chain. For example, Laminin-511 contains an α5 chain, a β1 chain, and a γ1 chain, Laminin-411 contains an α4 chain, a β1 chain, a γ1 chain. The nucleotide sequences and amino acid sequences of laminins are registered in GenBank, ENBL, DDBJ: laminin α5 nucleotide sequence (NM_005560) α5 amino acid sequence (NP_005551), β1 nucleotide sequence (NM_002291) β1 amino acid sequence (NP_002282) γ1 nucleotide sequence (NM_002293) γ1 amino acid sequence (NP_002284) α4 nucleotide sequence (NM_001105206) α4 amino acid sequence (NP_001098676).

The fragments used in the current innovation are Laminin 411-E8 fragment and laminin 511-E8 fragment. Access to highly purified products of both could be purchased from Wako company and Nippi company but not limited to this source. Laminin 511 E8 fragment was obtained by elastase digestion, leading to coiled-coil domain of laminin heterotrimer and three LG domain in C-terminal of the α5 chain (Taniguchi et al. J Biol Chem. 284:7820-7831, 2009). E8 fragment means an integrin-binding domain composing coiled-coin domain from three laminin sub-chains. Therefore, it is preferable that an integrin-binding domain is included in laminin fragment for our innovation. The Laminin 511 fragment sequence used in current innovation was based on sequence from E8 fragments from Laminin 511 and laminin 512. Similarly, Laminin 411 fragment used in our current innovation was made using the same method with that of Laminin 511 E8 fragment.

The dentin and/or pulp diseases treating drugs provided by our innovation include integrin-binding fragments from Laminin 411/511, porous hydroxyapatite or type I collagen (recombinant or naturally derived).

There are direct contact between the dentin and/or pulp diseases treating drugs provided by our innovation and cells, hence, it is possible to use our fragments for direct pulp capping to induce dentin regeneration. Dosage form could be solution type (injection type, infusion type, coating type), transdermal absorption type, granules type, fine granules type, powder type, tablet type or ointment type.

There is no limit regarding the dosage of fragments used for medical purpose. Proper concentration should be selected based on the progressing of caries, depth of dentin or pulp injuries, age and dosage type. For laminin fragment, a dry weight of which between 1 ng and 100 ng could be used each time.

The drug provided by current innovation is a type of dentin and/or pulp diseases treatment or preventive therapy. For selection of a carrier of this drug to be used in pulp capping, it is preferable to choose porous hydroxyapatite and type I collagen, or at least one of them. For example, to make the mixture of laminin fragment with carrier, one could first put 25 mg of the carrier (hydroxyapatite or type I collagen) into a syringe, then add 5-50 µg/30 µL of laminin fragment solution (dissolved in saline) dropwise to the carrier powder to finally make a mixture of laminin fragment with carrier. This mixture could be used as a pulp capping reagent. This pulp capping reagent may be used in unintended pulp horn exposure due to cavity preparation, or in uninfected exposed pulp, as a type of dentin formation inductive material. The final concentration of laminin fragment to be used in the treatment of dentin and/or pulp diseases or in the prevention of dental diseases should be over 1-100 nM.

The inventors showed for the first time the integrin binding fragments of laminin (Laminin 411 E8 fragment and Laminin 511 E8 fragment) were able to promote the proliferation and differentiation of odontoblast-like cells. Specifically, it is showed that cells cultured on laminin fragments proliferated much quickly than that on control or vitronectin-coated surface. The promotion of proliferation and differentiation of odontoblast-like cells was evidenced by an increase of ITGA1, ITGA5, ITGAV, ITGB1 and ITGB5 mRNA expression level on Laminin 411 E8 fragment, and ITGA1, ITGA3, ITGA5, ITGA6, ITGAV, ITGB1 and ITGB5 mRNA expression level on Laminin 511 E8 fragment. Based on the findings, Laminin 511 and Laminin 411 could enhance the expression of integrins in odontoblast-like cells, therefore, it is suggested they could be used as a special reagent for promoting the hard tissue formation in tooth.

Adherent cells in suspension will not spread and polarize, they only spread when cultured on suitable substrates where they rapidly reorganize membranes and cytoskeletons. The ability of an adherent cell to spread has important implications: flattened and spread human mesenchymal stem cells underwent osteogenesis, whereas un-spread round cells became adipocytes. Similarly, in the culture of odontoblast-like cells, dentin specific markers are activated in well spread and polarized cells. To confirm whether it is osteogenic or odontogenic differentiation, bone or tooth specific markers are used.

The inventors clarified laminin fragments promoted the late stage differentiation of cells. BSP is an early marker of osteoblast differentiation, OPN were promoted in the proliferation and differentiation process of osteoblast. OCN plays an important role in the regeneration of reversible pulpitis, it is expressed in mineralization front or penvascular sites instead of normal tissues (Abd-Elmeguid A et al J Endod 39: 865-72, 2013). Importantly, BSP and OPN were found to be mainly expressed in reparative dentin (Moses K D et al Eur J Oral Sci 114: 216-22, 2006). Based on the results, it is suggested integrin binding fragments derived from laminin induced the formation of reparative dentin. According to the findings of our innovation, reagents containing the integrin binding fragment derived from Laminin 411 can be used as a tooth hard tissue formation inductive drug due to its ability to induce the expression of OCN, BSP and OPN, which are important proteins to be found in reparative dentin.

The innovators showed integrin binding fragment derived from Laminin 511 E8 fragment could significantly enhance the odontogenic differentiation of MDPC-23 cells. This was evidenced by the up-regulation of DMP-1, DSPP, OPN and OCN in cells cultured on Laminin 511 E8 fragment. These four types of non-collagenous proteins were reported to be involved in the initiation and regulation of oriented crystallization of hydroxyapatite. Especially, DSPP is a protein that directs the transformation from pre-dentin to dentin: loss of DSPP leads to failure of dentin maturation (Sreenath T et al J Biol Chem 278: 24874-24880, 2003). Based on the results of our innovation, it is suggested reagents containing Laminin 511 E8 fragment may be used to induce the hard tissue formation of tooth as they significantly promoted the expression of odontogenic markers (DMP-1, DSPP, OPN and OCN).

Alizarin red staining is a method to detect the mineralization in osteoblast/odontoblast culture. The innovators confirmed the acceleration of mineralization in cells cultured on integrin binding fragments derived from laminin E8 fragments in the presence of osteogenic media including β-GP, Ascorbic acid and dexamethasone.

[Method for Making Tooth Hard Tissue Transplant]

We provide the method by combining two steps of cultivation. First, culturing cells on integrin binding fragments derived from Laminin 411 E8 and/or Laminin 511 E8 fragments, second, addition of mineralization inductive reagents mentioned in [0029].

The odontoblasts used in current innovation may be derived from the peripheral area of dental pulp, or dental pulp, or odontoblasts differentiated from stem cells of other tissues. Stem cells may be from dental pulp stem cells, dental papillae stem cells, bone marrow stromal cells, mesenchymal stem cells, hemopoietic stem cells, embryonic stem cells, or iPS cells. Based on the purpose of treatment, odontoblasts used in current innovation may be generated autogenically or allogenically.

In the current innovation, proliferation and differentiation of odontoblasts was induced by culturing on integrin binding fragments derived from Laminin 411 and/or laminin 511. This cell culture mixture, as a type of cell composition, could be transplanted into exposed pulp caused by caries or injuries as a treatment and/or preventative therapy in dentin or dental pulp diseases. The composition of culture substrates (Laminin 411 E8 and/or Laminin 511 E8) could be adjusted according to purposes.

Moreover, with increase of culturing time, the cell culture mixture mentioned above can be induced to further differentiation, that is the mineralization of matrix secreted by odontoblasts. The main organic component of odontoblast secretion is type I collagen, which could be induced to form mineralized nodules.

The tooth hard tissue forming transplant made by our innovation can be placed on exposed pulp caused by dental caries or injuries. This transplant is a mixture of odontoblast and its mineralized nodules, which could easily be attached to the pulp exposure site. Once the transplant is firmly attached to the exposure site, it induces the local tissues to secret self-assembled wound healing factors, which help the exposed pulp to close and achieve the treatment purpose. Moreover, cell sheet collected from odontoblasts cultured on transplantable substrates could also be used for treatment of exposed pulp caused by dental caries or injuries.

Regarding method, it is possible to simply coat the integrin binding fragments derived from Laminin 411 E8 or Laminin 511 E8 fragments. In detail, the coating method composed of addition of PBS diluted laminin fragments solution to cell culture plates or dishes under 4° C.-37° C. overnight. There is no limitation for the coating density, the range between 1-8 µg/cm$^2$ should be fine. The coating density for Laminin 411 E8 fragment is preferable to be 1 µg/cm$^2$, while that for Laminin 511 E8 fragment is preferable to be 8 µg/cm$^2$. Selection of above density was due to the significant high proliferative activity of MDPC-23 cells cultured on those substrates.

Besides coating, the two fragments could also be added into the cell culture media. The final concentration for both may be from 0.1 µg/mL to 3 µg/mL, however, no limitation was exerted.

There is also no limitation with regard to the culture substrates, be it non-coated culture plates or tissue culture treated plates. For both types of substrates, good results could be obtained for adherent cell culture. Meanwhile, there are no limitations for property or shape of culture substrates, for example, it can be glass or plastic dish, flask, multi-well plates, culture slides and culture bag etc. The culture substrates may be made from polystyrene, glass and acrylic etc.

Regarding the mineralization reagents, at least one reagent from β-GP, ascorbic acid, and dexamethasone should be included. The timing for addition of mineralization reagents is not limited to a specific time, it could be in the beginning, on the second day, on the third days, or after four days, it could also be before or after cell reaching confluence.

With regard to the cell culture media, those that are suitable for culturing odontoblasts may be fine. For example, it could be MEM, DMEM or M199 etc.

Detailed explanation of the current innovation is described taking the following content as an example. The current innovation is not limited to the contents given out below.

Experiment 1

Laminin 411 Fragment (Materials and Methods)
MDPC-23 Cell

MDPC-23 cell is kindly provided by Prof. Jacques E Nor from University of Michigan. The cells were grown in Dulbecco modified eagle medium (DMEM, D5796, Sigma) supplemented with 5% fetal bovine serum (FBS, 10270-106, Gibco) (maintenance media) at 37° C. in a humidified atmosphere containing 5% CO2. For the induction of differentiation and mineralization, reagents were added on the day cells reaching confluence and changed every two days. The mineralization reagents include 5% FBS, 10 mM β-glycerophosphate (191-02042, Wako), 50 µg/mL ascorbic acid (013-19641, Wako), 100 nM dexamethasone (D2915, Sigma) and DMEM.

Laminin 411 Coating iMatrix-411 (herein referred to as LN411-E8) (iMatrix-411, Nippi, No. 892041) was diluted by PBS and coated to tissue culture treated polystyrene (TCPS, vacuum plasma treated, hydrophilic, water contact angle 38°±9° or nontissue culture treated polystyrene (12-well plate, 351143, Falcon) (non-PS, water contact angle 84°±4°). The solution was kept on the plates for 2 hrs at 37° C. MDPC-23 cells were inoculated onto the LN411-E8 coated or non-coated culture plates. The specific protocol for making TCPS plates from non-tissue culture treated polystyrene (Non-PS) is described elsewhere (Rostam H M et al Immunobiology 221: 1237-1246, 2016). mRNA expression of bone markers, dentin markers and integrins was evaluated, moreover, alkaline phosphatase activity was also investigated. The coating volume for 96-well plate and 12-well plate was 50 µL and 400 µL, respectively.

Cell Counting Kit-8 Assay

Viable cells on LN411-E8 was quantified using CCK-8 (Dojindo) kit.

A series of coating density for LN411-E8 was coated into 96-well plate and cells were inoculated at the number of 1×10$^3$/well. After 48 hours of cultivation, the tetrazolium salt WST-8 was added to each well (10 µL/well) for 1 hour and 45 minutes, thereafter, the WST-8 is reduced by dehydrogenases in cells to give an orange color formazan, which is soluble in culture medium. The amount of the formazan dye generated by dehydrogenases in cells is directly proportional to the number of living cells. Absorbance was read at 450 nm. For cell proliferation experiment, cell seeding number was adjusted to 0.5×10$^3$/well, and absorbance was read on day two, day three, and day five.

Alkaline Phosphatase Activity (ALP Activity)

Cells (1.25×10$^4$/well) were seeded into LN411-E8 coated 12-well plates (Non-PS and TCPS). Mineralization reagents were added on day five. At day eight, ALP activity was quantified by LabAssay ALP kit (Wako). The activity was divided by protein amount (µg), which was evaluated using Pierce Protein Assay.

Gene Expression

Cells were seeded and mineralization reagents were added in the same manner as described in [0044]. At day seven, Trizol reagent (15596018, Life Technologies) was used to lysate cells and acid-guanidinium-phenol-chloroform (AGPC method) was employed to purify RNA. RNA was quantified using NanoDrop 1000 (Thermo Fisher Scientific) and Oligo(dT) primer (Invitrogen) was used to synthesize cDNA. After that, the mRNA expression level of dentinogenesis markers such as OCN, BSP, OPN, ALP, DMP-1, DSPP and Runx-2 together with several integrins ITGA1, ITGA3, ITGA5, ITGA6, ITGAV, ITGB1 and ITGB5 was investigated using real time RT-PCR (LightCycler Nano, Roche). β-actin was taken to be the internal control. Primer sequences are shown in Table 1.

TABLE 1

| Gene name | Forward (5'to 3') | Backward (5' to 3') | Fragment size (bp) | Tm |
|---|---|---|---|---|
| OCN | AGCTCAA CCCCAAT TGTGAC (SEQ ID NO: 1) | AGCTGTG CCGTCCA TACTTT (SEQ ID NO: 2) | 190 | 55 |

TABLE 1-continued

| Gene name | Forward (5' to 3') | Backward (5' to 3') | Fragment size (bp) | Tm |
|---|---|---|---|---|
| BSP | CTGCTTTAATCTTGCTCTG (SEQ ID NO: 3) | CCATCTCCATTTTCTTCC (SEQ ID NO: 4) | 211 | 55 |
| OPN | TTTCCCTGTTTCTGATGAACAGTAT (SEQ ID NO: 5) | CTCTGCTTATACTCCTTGGACTGCT (SEQ ID NO: 6) | 228 | 55 |
| ALP | GGAAGGAGGCAGGATTGACCAC (SEQ ID NO: 7) | GGGCCTGGTAGTTGTTGTGAGC (SEQ ID NO: 8) | 338 | 55 |
| DMP-1 | CGTTCCTCTGGGGGCTGTCC (SEQ ID NO: 9) | CCGGGATCATCGCTCTGCATC (SEQ ID NO: 10) | 577 | 60 |
| DSPP | TCAATGGCGGGTGCTTTAGA (SEQ ID NO: 11) | TGCTCACTGCACAACATGAAGA (SEQ ID NO: 12) | 111 | 62 |
| Runx-2 | CCACAGAGCTATTAAAGTGACAGTG (SEQ ID NO: 13) | AACAAACTAGGTTTAGAGTCATCAAGC (SEQ ID NO: 14) | 87 | 55 |
| ITGA1 | TCAACGTTAGCCTCACCGTC (SEQ ID NO: 15) | CAGGGATCGTCTCATTGGCA (SEQ ID NO: 16) | 396 | 59.9 |
| ITGA3 | GAAAGGCTGACCGACGACTA (SEQ ID NO: 17) | TGCGTGGTACTTGGGCATAA (SEQ ID NO: 18) | 108 | 66 |
| ITGA5 | GAAGGGACGGAGTCAGTGTG (SEQ ID NO: 19) | TGAATGGTGCTGCACTGGAT (SEQ ID NO: 20) | 127 | 66 |
| ITGA6 | CTGAGATCCACACTCAGCCG (SEQ ID NO: 21) | GCATGGTATCGGGGAACACT (SEQ ID NO: 22) | 126 | 66 |
| ITGAV | ATAAAGCGCGGATGGCAAAG (SEQ ID NO: 23) | CTCACCCGAAGATAGGCGAC (SEQ ID NO: 24) | 213 | 64.9 |
| ITGB1 | ACAAGAGTGCCGTGACAACT (SEQ ID NO: 25) | AGCTTGATTCCAAGGGTCCG (SEQ ID NO: 26) | 325 | 59.9 |
| ITGB5 | CACGGTCCATCATCTCTCGG (SEQ ID NO: 27) | CATGGAGAGGGAGAGGTCCA (SEQ ID NO: 28) | 281 | 62.8 |
| β-actin | AACCCTAAGGCCAACAGTGAAAAG (SEQ ID NO: 29) | TCATGAGGTAGTCTGTGAGGT (SEQ ID NO: 30) | 241 | 53 |
| BMP-4 | CAGGGCCAACATGTCAGGAT (SEQ ID NO: 31) | TGGCGACGGCAGTTCTTATT (SEQ ID NO: 32) | 188 | 59.9 |

BMP-4 primer was used in real time RT-PCR in experiment 2 but not experiment 1. ITGAV primer was only used real time RT-PCR for experiment 1.

Statistical Analysis

Results were expressed as mean±standard deviation. Statistical analysis was conducted using post hoc Tukey's HSD test. A value of $p<0.05$ was considered statistically significant.

Coating Density for Laminin 411 Fragment

Sound cell proliferative activity was observed on LN411-E8 coated between 1 and 8 μg/cm². However, the optimal coating density was found to be at 8 μg/cm². The following experiments were conducted using this coating density.

Cell Morphology

Figure 2A:
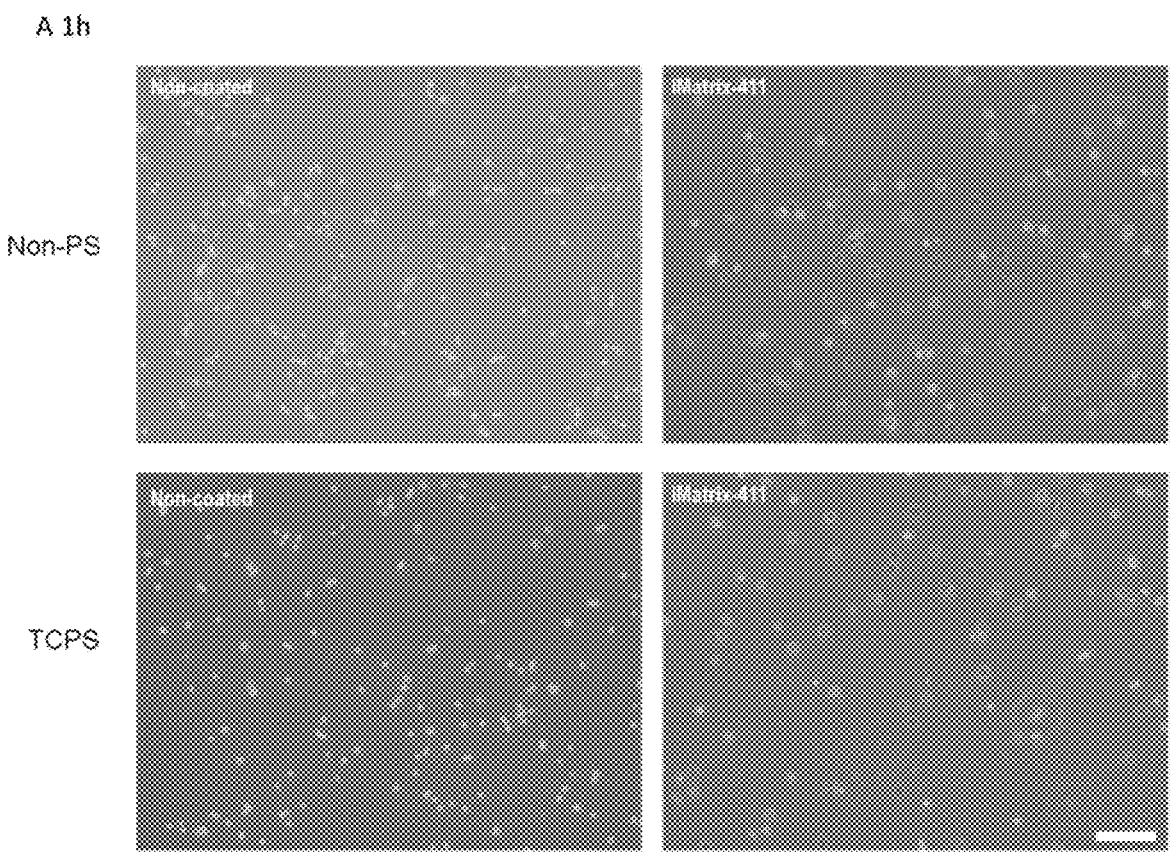
FIG. 2A The micrograph indicating the cell shape of the MDPC-23 cell one-hour after the dissemination in the surface (Non-coated) that it is not coated surface (iMatrix-411) and LN411-E8 coated LN411-E8. Non-PS: Polystyrene, TCPS: for the non-tissue culture Polystyrene for the tissue culture. The scale bar is 200 µm.

Cells started to flatten as early as 1 h when they were inoculated to LN411-E8-modified polystyrene (Non-PS and TCPS), while those on noncoated controls were still round, spot-like in shape (FIG. 2A). There were no differences of cell morphology between noncoated Non-PS and noncoated TCPS.

Figure 2B:
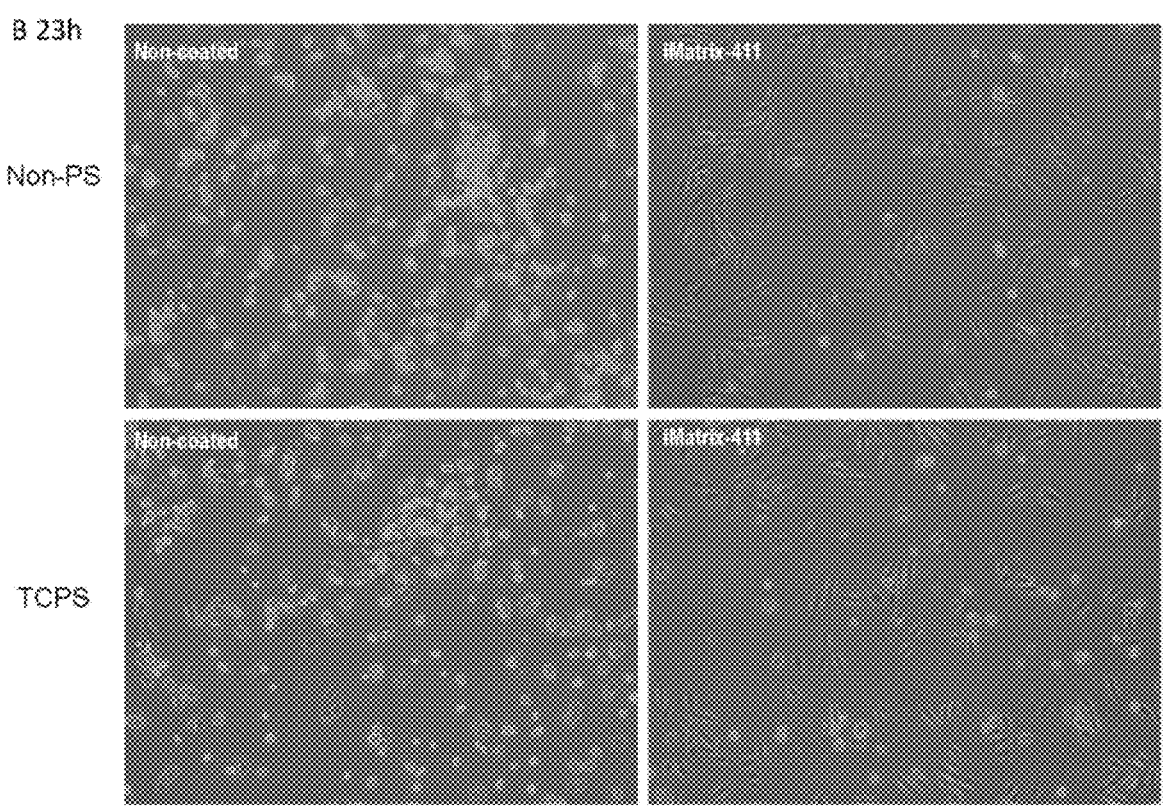
FIG. 2B The micrograph indicating the cell shape of the MDPC-23 cell 23-hour after the dissemination.
Figure 2C:
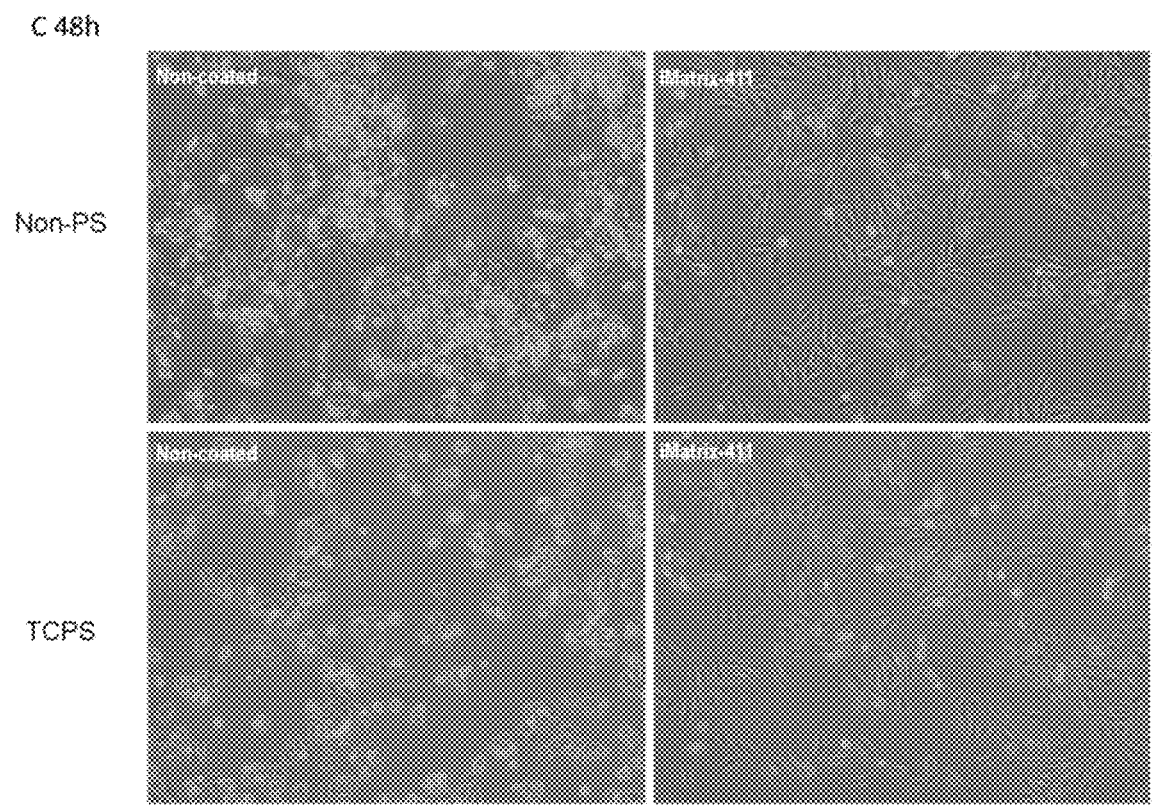
FIG. 2C The micrograph indicating the cell shape of the MDPC-23 cell 48-hour after the dissemination.

At 23 h and 48 h, differences among surfaces were even more evident. Cells on LN411-E8 modified Non-PS or TCPS adopted spindle shape were elongated fibroblast-like in appearance (FIGS. 2 B & C), displaying larger spreading area compared to noncoated counterparts: although the cells could also attach to noncoated Non-PS and noncoated TCPS, they appeared in a smaller, more compact, and rounded morphology.

Cell Proliferation.

Figure 3:
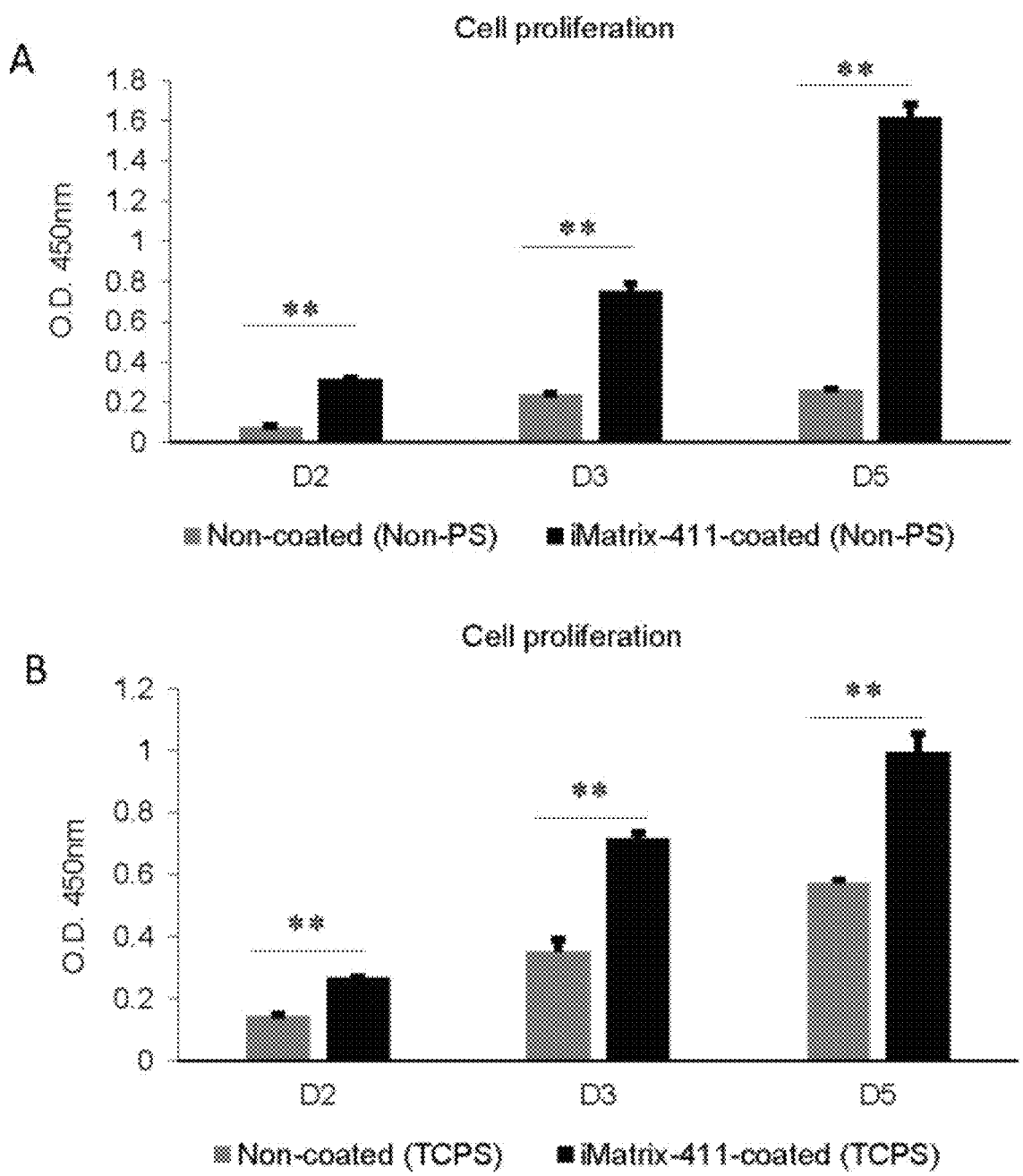
FIG. 3 (A), on surface (iMatrix-411) and the LN411-E8 culture start second day coated LN411-E8 each of polystyrene for the non-tissue culture and (B) polystyrene for the tissue culture in the surface (Non-coated) which is not coated, is the cell proliferation activity of the MDPC-23 cell on the third day and the fifth day. (**$p<0.01$ by post hoc Tukey HSD test)

On day two, day three and day five, cell viability on LN411-E8 modified Non-PS (FIG. 3a. D2: 0.32±0.00 of iMatrix-411 versus 0.08±0.01 of control; D3: 0.76±0.04 of iMatrix-411 versus 0.24±0.00 of control; D5: 1.62±0.07 of iMatrix-411 versus 0.26±0.01 of control) or TCPS (FIG. 3(b). D2: 0.27±0.00 of iMatrix-411 versus 0.15±0.00 of control; D3: 0.72±0.02 of iMatrix-411 versus 0.35±0.04 of control; D5: 0.99±0.06 of iMatrix-411 versus 0.57±0.01 of control) was significantly elevated compared with noncoated controls. Furthermore, cells in noncoated Non-PS exhibited limited growth (FIG. 3(a) grey), while those grown on noncoated TCPS (FIG. 3(b) grey) adopted faster rate of growth.

Alkaline Phosphatase Activity (ALP Activity)

Figure 4:
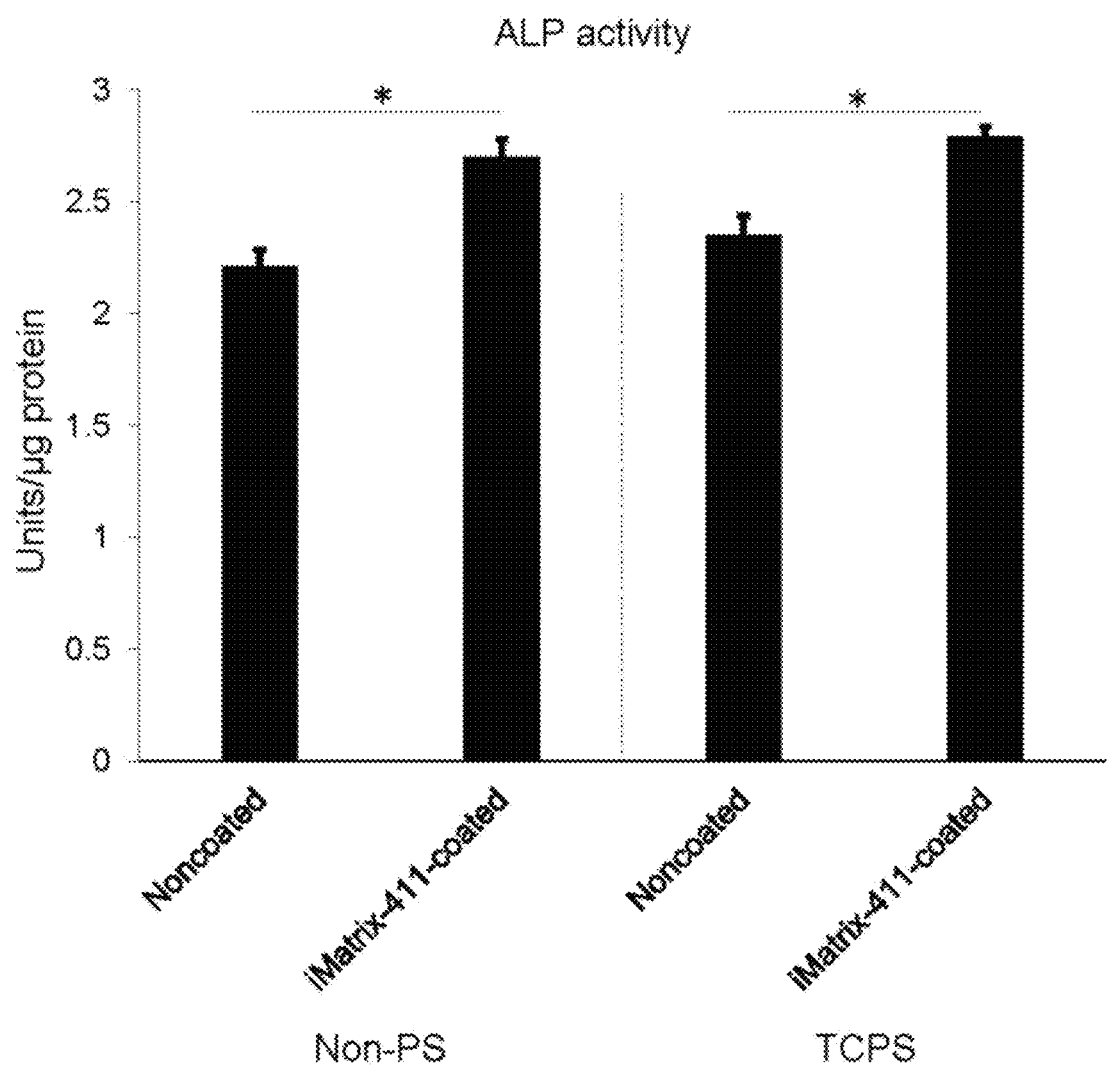
FIG. 4 The alkaline phosphatase activity in the MDPC-23 cell three days after the calcified nutrient medium addition. About Non-PS (polystyrene for the non-tissue culture) and TCPS (polystyrene for the tissue culture), I show LN411-E8 by a comparison between surface (Non-coated) and coated surface (iMatrix-411) that is not coated each. (*$p<0.005$ by post hoc Tukey HSD test)

Cells grown on iMatrix-411 displayed significant higher ALP activity compared with those on noncoated controls (FIG. 4). This enhancing effect applies to both Non-PS (FIG. 4 left to dotted line: 2.70±0.08 Units/μg protein of iMatrix-411 versus 2.21±0.08 Units/μg protein of control) and TCPS (FIG. 4 right to dotted line: 2.79±0.05 Units/μg protein of iMatrix-411 versus 2.35±0.08 Units/μg protein of control). However, ALP activity of cells seeded on noncoated TCPS did not differ with that on noncoated Non-PS (p>0.05).

Osteo/Odontogenic Markers

The mRNA expression levels of seven types of osteo/odontogenic markers were evaluated.

The control group (noncoated Non-PS) was set for the mRNA expression baselines (relative expression values at 100%).

Figure 5A:
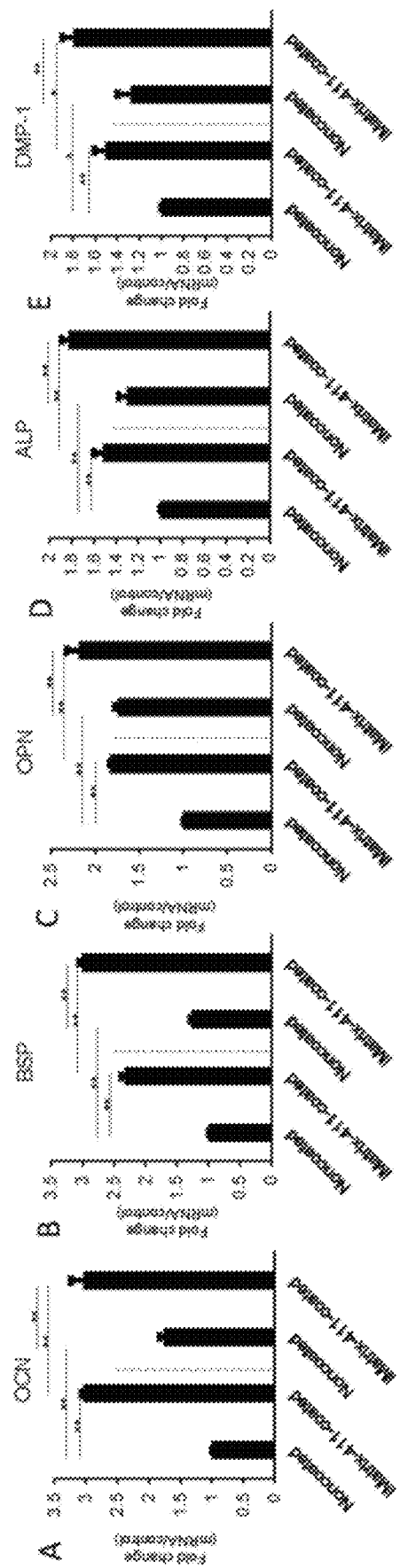
FIGS. 5A, 5B and 5C Bone/odontogenesis marker expression in the calcified nutrient medium addition two days later MDPC-23 cell and integrin expression. The left side of the dotted line of each panel is Non-PS, and the right side is TCPS. The gene expression level that was significantly reinforced in the MDPC-23 cell which I multiplied on LN411-E8 coating Non-PS or TCPS was observed with next bone/odontogenesis marker. OCN ($3.03\pm0.03$ times increase in iMatrix-411 coating Non-PS), BSP ($2.34\pm0.05$ times increase in iMatrix-411 coating Non-PS), OPN ($1.83\pm0.01$ times increase in iMatrix-411 coating Non-PS), ALP ($1.52\pm0.08$ times increase in iMatrix-411 coating Non-PS), DMP-1 ($1.51\pm0.10$ times increase in iMatrix-411 coating Non-PS), DSPP ($1.26\pm0.08$ times increase in iMatrix-411 coating Non-PS), Runx-2 ($1.24\pm0.04$ times increase in iMatrix-411 coating Non-PS). About the integrin, the gene expression level that was significantly reinforced in ITGA1 ($2.17\pm0.05$ times increase in iMatrix-411 coating Non-PS) was observed. (*$p<0.05$, **$p<0.01$, post hoc Tukey HSD test)

OCN displayed an increase of 3.03 times for MDPC-23 cells on iMatrix-411-modified Non-PS surface (FIG. 5A(A) left to dotted line). Moreover, seeding of cells in noncoated TCPS remarkably enhanced its expression to 1.77-fold compared with noncoated Non-PS (FIG. 5A(A) first and third bar).

BSP, expressed by both osteoblast and odontoblast, demonstrated a 2.34-fold increase for the cells cultured on iMatrix-411 coated Non-PS compared with control (FIG. 5A(B) left to dotted line). Meanwhile, seeding of cells into TCPS could further elevate its expression by 1.27-fold (FIG. 5A(B) first and third bar).

Both OPN (FIG. 5A(C): 1.83-fold increase versus control) and ALP (FIG. 5A(D): 1.52-fold versus control) expression levels for the cells on iMatrix-411-modified Non-PS were significantly higher than noncoated group as well. Similar to OCN, inoculation of cells into noncoated TCPS significantly enhanced the mRNA expression of both genes (OPN: 1.75-fold of increase in noncoated TCPS; ALP: 1.30-fold of increase in noncoated TCPS).

Figure 5B:
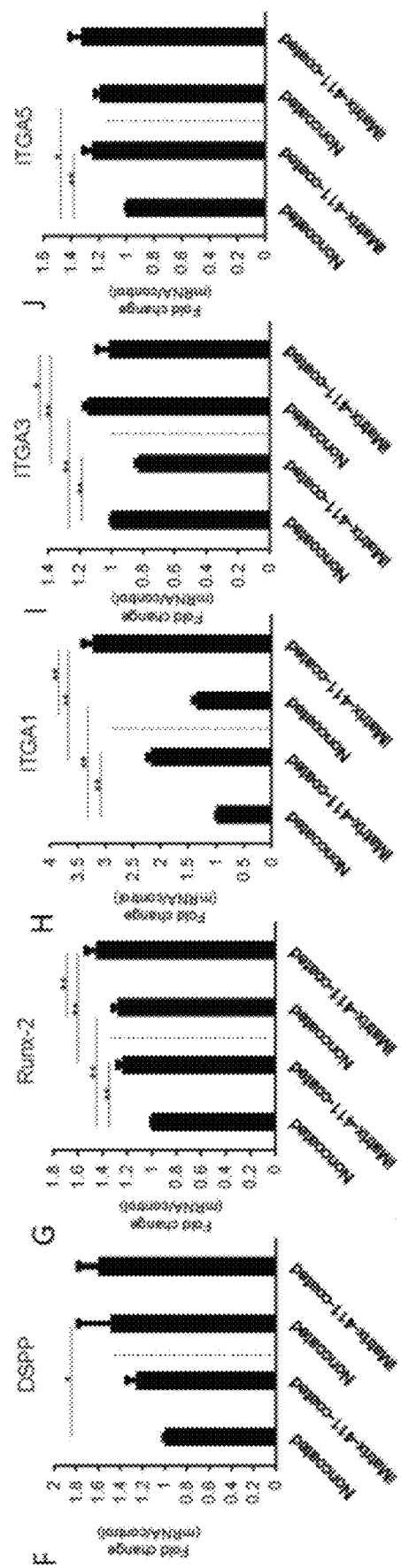

For the remaining three genes, DMP-1 (FIG. 5A(E)), DSPP (FIG. 5B(F)) and Runx-2 (FIG. 5B(G)), there was only slight increment of expression on iMatrix-411 compared with control. Consistent with the above genes, gas plasma-treated noncoated TCPS promoted expression of these three genes compared with noncoated Non-PS.

Except for ITGA3 and ITGA6, expression of the other five integrins was found to be promoted by iMatrix-411. Specifically, ITGA1 was the one that was enhanced to the largest extent (2.17-fold increase, FIG. 5B(H)), also, cells cultured in noncoated TCPS promoted its expression to 1.35-fold (FIG. 5B(H) first and third bar).

Figure 5C:
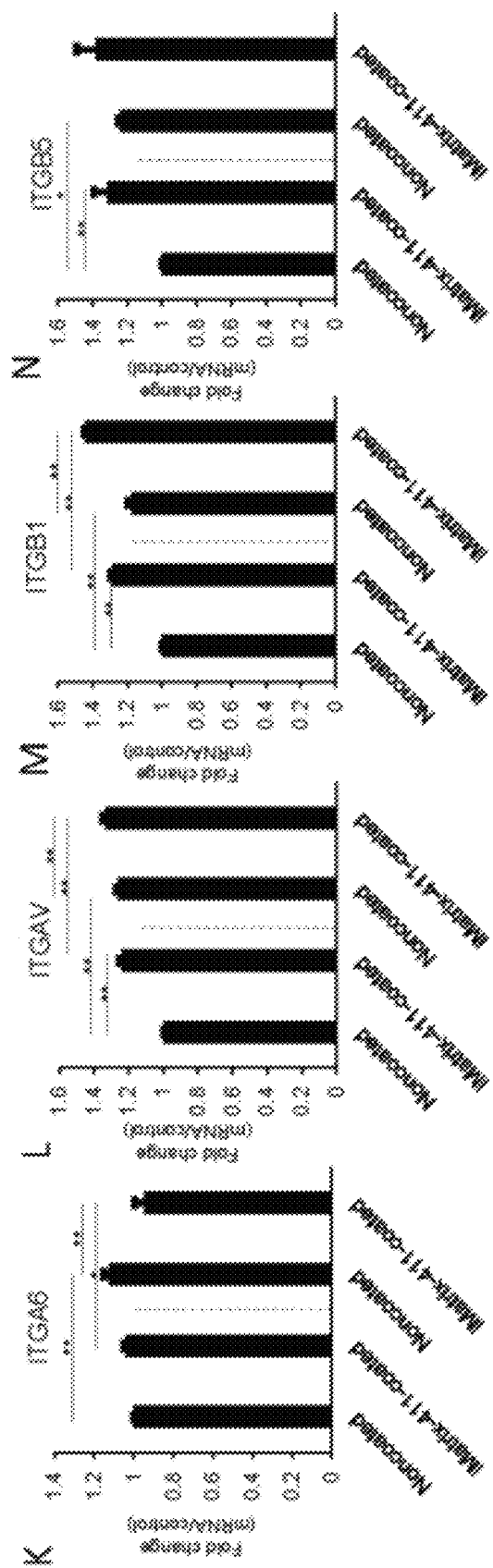

With regard to ITGA5, ITGAV, and ITGB1, they were promoted by iMatrix-411 to comparable levels in Non-PS (FIG. 5B(J) 1.25-fold, FIG. 5B(L) 1.24-fold, and FIG. 5C(M) 1.29-fold). Similarly, mRNA expression of the three integrins was elevated by seeding cells into noncoated TCPS compared with noncoated Non-PS. ITGB5, a reported fibronectin receptor, was enhanced by iMatrix-411 to 1.32-fold in Non-PS (FIG. 55C(N) left to dotted line). Seeding of cells to TCPS also augmented ITGB5 expression by 1.24 times, while no difference was detected in noncoated TCPS and iMatrix-411-coated TCPS (FIG. 5C(N) right to dotted line). In contrast, ITGA3 was downregulated by iMatrix-411 in Non-PS (0.83-fold) (FIG. 5B(I) left to dotted line); however, seeding cells to TCPS slightly upregulated its expression by 1.15-fold. Regarding ITGA6, there was no difference in expression between noncoated and iMatrix-411-coated Non-PS (FIG. 5C(K) left to dotted line); interestingly, in TCPS, it was found that the expression of ITGA6 was mildly suppressed by iMatrix-411 (FIG. 5C(K) right to dotted line).

Experiment 2

Laminin 511 Fragment (Materials and Methods)

MDPC-23 cells were cultured in the same manner as described in Experiment 1. Laminin 511 E8 fragment was purchased from Nippi company. For comparison with other ECM protein, vitronectin (Peprotech, 140-09) was also used.

Detailed information is provided in Experiment 1 with regard to protein coating, CCK-8 assay (optimal density, cell proliferation experiment), alkaline phosphatase activity, gene expression and statistical analysis. However, in Experiment 2, both LN511-E8 and vitronectin were used for cell culture. Also, in the cell proliferation assay, data were collected on day one, day two and day four. At last, tissue culture polystyrene (TCPS) culture plates were not used in Experiment 2.

Alizarin Red Staining

At the end of the culture period (day 8), the cell monolayer was fixed with 10% neutral formalin solution (060-01667, Wako) for 20 minutes and stained with 1% alizarin red solution (pH=4.1; 011-01192, Wako) in the dark for 5 to 10 minutes in an incubator under 37C. The mineralized nodules were imaged photographically before the dissolution of the bound dye with cetylpyridinium chloride (CPC, 10% in distilled water [C0732-100G, Sigma-Aldrich]), and the quantification of the absorbance was spectrophotometrically determined at 570 nm.

Coating Density for LN511-E8 and Vitronectin

Figure 6:
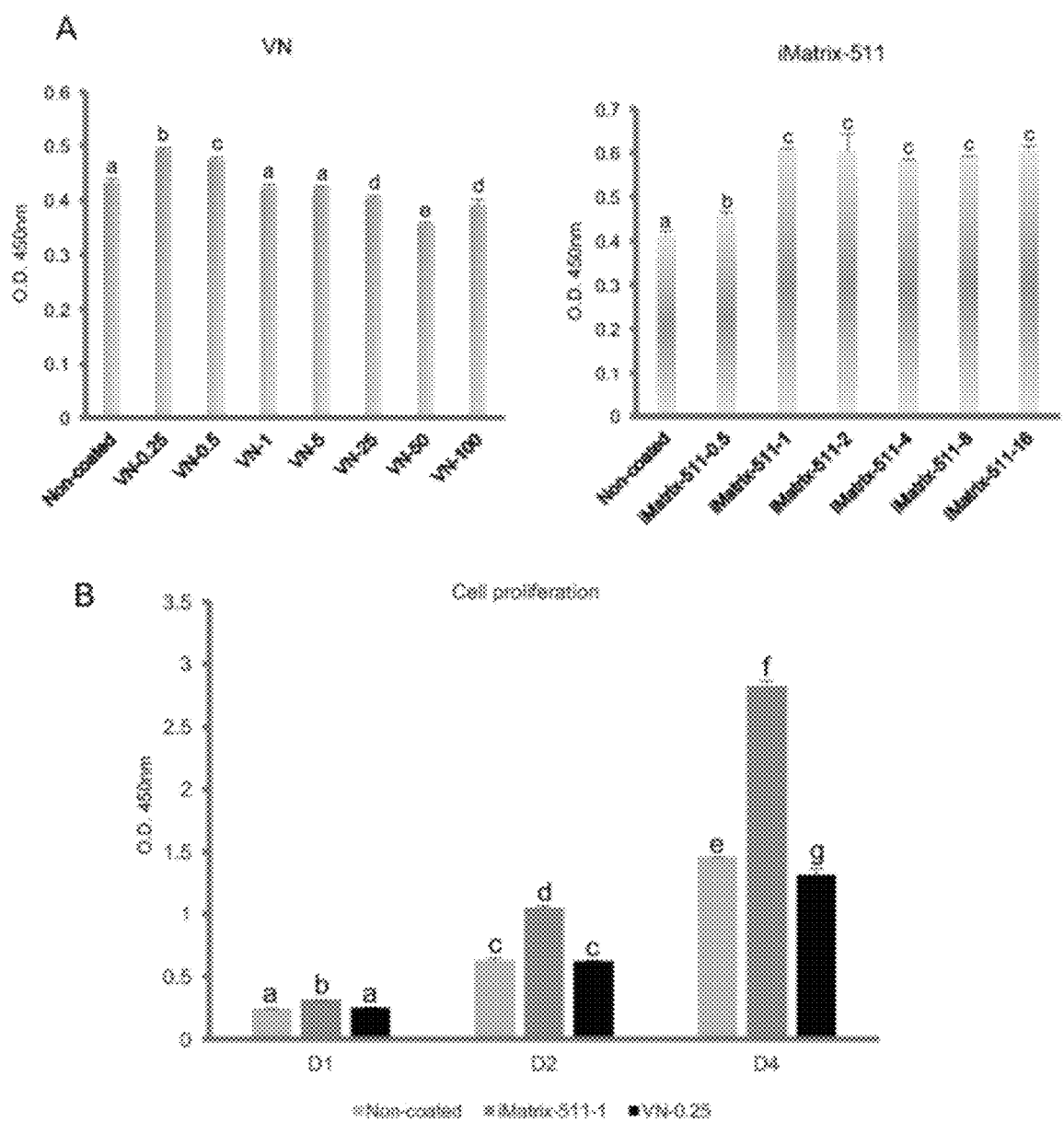
FIG. 6 (A) the cell proliferation activity of the MDPC-23 cell in the different coating density of LN511-E8. The number (0.25, 0.5, 1, 5, 25, 50, 100, 0.5, 1, 2, 4, 8, 16) following VN or iMatrix-511 is coating density (μg/cm2) of VN or N511-E8. Different letter a-e on the bar shows the significant difference of each panel (p<0.05, post hoc Tukey HSD test). (B) the cell proliferation activity of the MDPC-23 cell of on the culture start first day in non-coated surface (Non-coated), LN511-E8 coated surface (iMatrix-511-1, coating density 1 μg/cm$^2$) and the VN coated surface (VN-0.25, coating density 0.25 μg/cm$^2$), the second day and the fourth day. Different letter a-g on the bar shows the significant difference of each panel (p<0.05, post hoc Tukey HSD test).

The CCK-8 assay was performed to determine the cell viability of MDPC-23 cells cultured on iMatrix-511 and VN with various coating density (FIG. 6A). The results showed that the viability of cells was slightly enhanced at a density of 0.25 mg/cm$^2$ of VN and decreased with the increase of density. As for iMatrix-511, the viability of cells exhibited a concentration-dependent increase trend and reached a plateau when the density was over 1 mg/cm$^2$. The optimal coating density for iMatrix-511 and VN was determined to be 1 mg/cm$^2$ and 0.25 mg/cm$^2$, respectively. The following experiments were all conducted using the optimal density for each protein.

Cell proliferation was evaluated using the CCK-8 assay (FIG. 6B). A significantly high proliferative activity in cells cultured on iMatrix-511 (day 1: 0.31±0.00 vs control: 0.25±0.00, P<0.01; day 2: 1.05±0.02 vs control: 0.63±0.02, P<0.01; day 4: 2.83±0.04 vs control: 1.45±0.00, P<0.01) was confirmed and persisted on the 3 days tested. No differences were detected between the control and VN groups for day 1 (0.25±0.01) or day 2 (0.62±0.01), indicating VN was not an adhesive for MDPC-23 cells. When it came to day 3, the cell number in VN (1.31±0.06, P<0.05) was even slightly decreased compared with the control.

Cell Morphology

Figure 7:
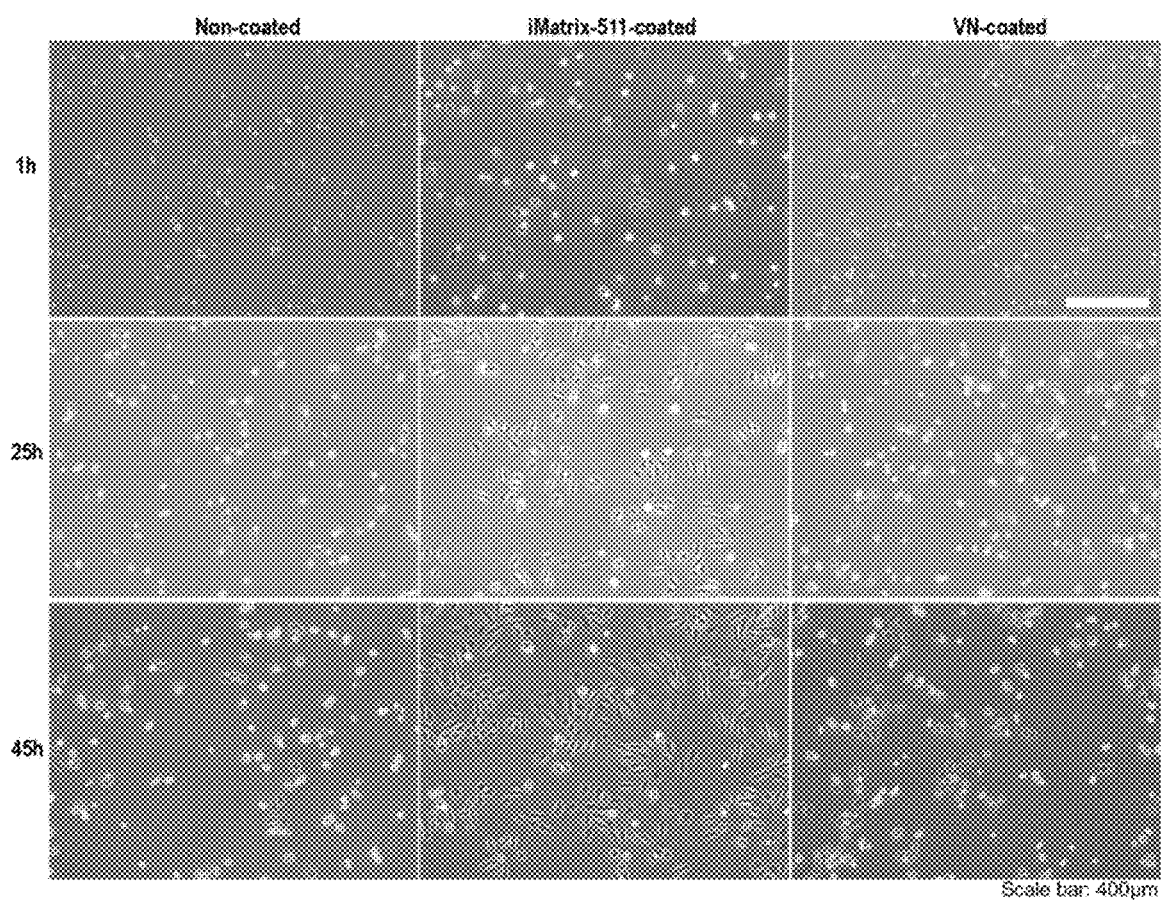
FIG. 7 It is the micrograph indicating the cell shape of the MDPC-23 cell of one hour (the upper section), 25 hours (the middle section) and 48 hours (the lower berth) after the culture start in non-coated surface (Non-coated), LN511-E8 coated surface (iMatrix-511-1) and the VN coated surface (VN-0.25).

Cell morphology observed by a light microscope suggested that MDPC-23 cells adhere preferentially to iMatrix-511 as early as 1 hour (FIG. 7 upper panel) when cells in the other 2 groups were still spherical in shape. It is clearly shown in the figure that cells started to form protrusions in iMatrix-511 at 1 hour. After 1 day, MDPC-23 cells had already spread well across the iMatrix-511 substrate (FIG. 7 middle panel). After 45 hours (FIG. 7 lower panel), the cells on iMatrix-511 continued to grow and exhibit a spindle shape, whereas most of the cells in the control and VN groups were still round.

mRNA Expression of Odontogenic Markers and Integrins

Figure 8:
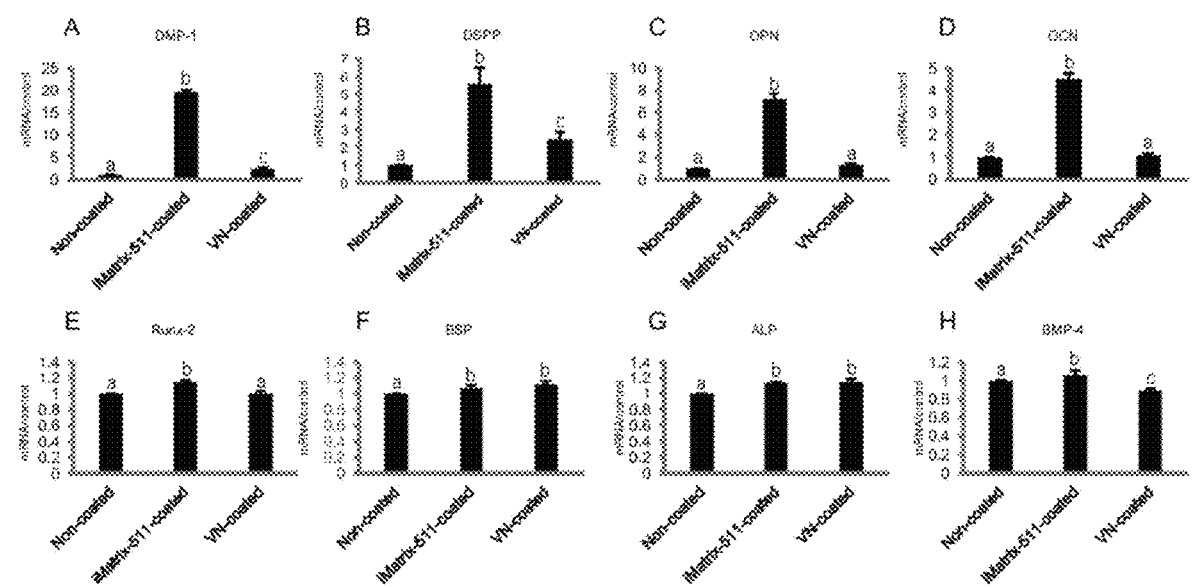
FIG. 8 A bone, the odontogenesis-specific gene expression (A-H) in the cell which I cultured at non-coated surface (Non-coated), LN511-E8 coated surface (iMatrix coated) and VN coated surface (VN-coated). The cell came to light by a calcified instruction nutrient medium for existence lower seven days of β-GP, AA and Dex. The odontogenesis-specific genetic mRNA expression was normalized for β-actin each bone. The different letter expresses the significant difference of each panel (p<0.05).
Figure 9:
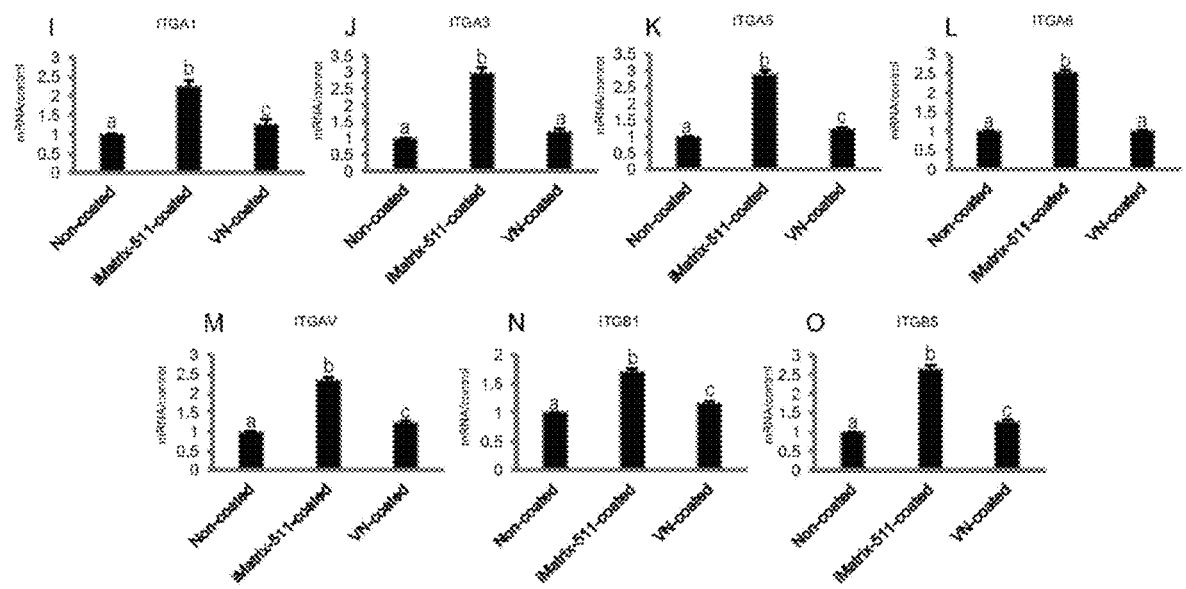
FIG. 9 The expression of integrin gene in the cell which I cultured at non-coated surface (Non-coated), LN511-E8 coated surface (iMatrix-511-coated) and VN coated surface (VN-coated) (I-O). The mRNA expression of each integrin gene was normalized for β-actin. The cell came to light by a calcified instruction nutrient medium for existence lower seven days of β-GP, AA and Dex. The mRNA expression of each integrin gene was normalized for β-actin. The different letter expresses the significant difference of each panel (p<0.05).

To investigate the effects of iMatrix-511 and VN on odontogenic differentiation and integrin expression profiles, quantitative RT-PCR analysis was performed. iMatrix-511 strongly enhanced the messenger RNA (mRNA) expression of 2 key odontogenesis related markers: dentin matrix protein-1 (DMP-1 [19.72±0.40-fold, P<0.01]) and dentin sialophosphoprotein (DSPP [5.61±0.91-fold, P<0.01]) (FIGS. 8A and B). In addition, 2 hard tissue forming— related markers, osteopontin (OPN [7.20±0.51-fold, P<0.01]) (FIG. 8C) and osteocalcin (OCN [4.53±0.24-fold, P<0.01]) (FIG. 8D), were also found to be augmented in cells cultured on iMatrix-511. Surprisingly, osteoblast markers such as Runt-related transcription factor 2 (Runx-2), bone sialoprotein (BSP), and ALP were only slightly up-regulated by iMatrix-511 (FIG. 8E-G). Moreover, the mRNA expression of bone morphogenetic protein 4 (BMP-4) (FIG. 8H), a novel odontogenic factor, was also only slightly enhanced in iMatrix-511. On the other hand, VN was found to promote the expression of DMP-1 (FIG. 8A, 2.33±0.30-fold, P<0.01) and DSPP (FIG. 8B, 2.45±0.39-fold, P<0.01), albeit to a much lesser extent than iMatrix-511. VN did not impact the expression of Runx-2 and BMP-4 but mildly elevated the expression of BSP and ALP.

iMatrix-511 up-regulated the expression of 7 types of integrins (ITGA1, ITGA3, ITGA5, ITGA6, ITGAV, ITGB1, and ITGB5) (FIG. 9I-O); the fold change was between 1.70 and 3.00. VN also promoted the expression of most integrins except for ITGA3 and ITGA6.

Mineralization Assay

Figure 10:
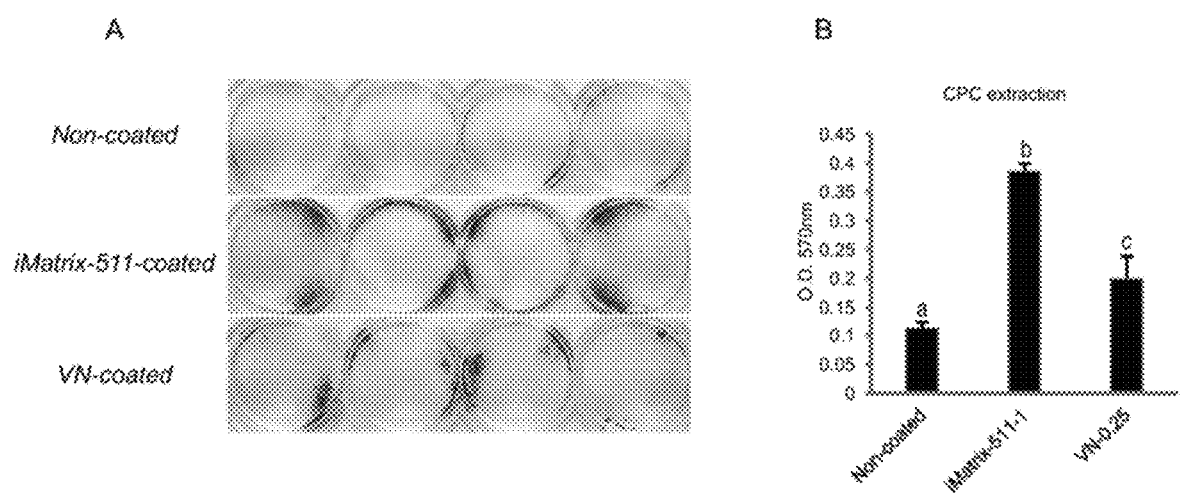
FIG. 10 The alizarin red dyeing quantified by CPC sampling method. (A) cultured MDPC-23 cell before the addition of the calcified instruction nutrient medium (β-GP, AA and Dex) for four days, and dyed it about calcification on the seventh day. (B) quantitative measurement of the alizarin red dyeing by the CPC extraction. The result expresses it as mean±SD. The different letter shows a significantly different thing between the letters (p<0.05).

To examine the effect of iMatrix-511 on odontogenic differentiation, we further assessed mineralized nodule formation by the alizarin red staining method throughout a period of 8 days of culture in the presence of mineralization media (b-GP, AA, and Dex). FIGS. 10A and B shows that after 4 days of exposure to the induction factors, iMatrix-511 acted as an effective mineralized nodule inducer compared with the control or VN. The CPC extraction further confirmed a 3.5-fold increase (P<0.01) in the staining intensity in iMatrix-511 compared with the control. Mineralization was also slightly promoted by VN (1.8-fold, P<0.01).

The invention claimed is:

1. A tooth dentin, pulp or pulp tissue composition for treating or preventing a disease, disorder, or symptom of a tooth dentin and/or pulp or pulp tissue, the composition comprising:
   a mixture of odontoblasts and mineralized nodules secreted from the odontoblasts,
   wherein the odontoblasts have been cultured on a coating which comprises an integrin binding fragment of Laminin such that mRNA expression levels of ITGA1, ITGA5, ITGAV, ITGB1, and ITGB5 in the odontoblasts are increased as compared with the odontoblasts which have not been cultured on the coating,
   wherein the Laminin is at least one of Laminin 511 and Laminin 411, the integrin binding fragment comprising an integrin-binding domain, and a coating density of the integrin binding fragment of the at least one of Laminin 511 and the Laminin 411 in the coating is 1 to 8 µg/cm$^2$, and
   wherein the composition is applicable to a tooth and able to treat or prevent the disease, disorder or symptom of the tooth dentin and/or pulp tissue including dental caries when applied to the tooth.

* * * * *

SEQUENCE LISTING

```
Sequence total quantity: 32
SEQ ID NO: 1            moltype = DNA  length = 20
FEATURE                 Location/Qualifiers
source                  1..20
                        mol_type = other DNA
                        organism = synthetic construct
SEQUENCE: 1
agctcaaccc caattgtgac                                                    20

SEQ ID NO: 2            moltype = DNA  length = 20
FEATURE                 Location/Qualifiers
source                  1..20
                        mol_type = other DNA
                        organism = synthetic construct
SEQUENCE: 2
agctgtgccg tccatacttt                                                    20

SEQ ID NO: 3            moltype = DNA  length = 19
FEATURE                 Location/Qualifiers
source                  1..19
                        mol_type = other DNA
                        organism = synthetic construct
SEQUENCE: 3
ctgctttaat cttgctctg                                                     19

SEQ ID NO: 4            moltype = DNA  length = 18
FEATURE                 Location/Qualifiers
source                  1..18
                        mol_type = other DNA
                        organism = synthetic construct
SEQUENCE: 4
ccatctccat tttcttcc                                                      18

SEQ ID NO: 5            moltype = DNA  length = 25
FEATURE                 Location/Qualifiers
source                  1..25
                        mol_type = other DNA
                        organism = synthetic construct
SEQUENCE: 5
tttccctgtt tctgatgaac agtat                                              25

SEQ ID NO: 6            moltype = DNA  length = 25
FEATURE                 Location/Qualifiers
source                  1..25
                        mol_type = other DNA
                        organism = synthetic construct
SEQUENCE: 6
ctctgcttat actccttgga ctgct                                              25

SEQ ID NO: 7            moltype = DNA  length = 22
FEATURE                 Location/Qualifiers
source                  1..22
                        mol_type = other DNA
                        organism = synthetic construct
```

```
SEQUENCE: 7
ggaaggaggc aggattgacc ac                                                    22

SEQ ID NO: 8            moltype = DNA   length = 22
FEATURE                 Location/Qualifiers
source                  1..22
                        mol_type = other DNA
                        organism = synthetic construct
SEQUENCE: 8
gggcctggta gttgttgtga gc                                                    22

SEQ ID NO: 9            moltype = DNA   length = 20
FEATURE                 Location/Qualifiers
source                  1..20
                        mol_type = other DNA
                        organism = synthetic construct
SEQUENCE: 9
cgttcctctg ggggctgtcc                                                       20

SEQ ID NO: 10           moltype = DNA   length = 21
FEATURE                 Location/Qualifiers
source                  1..21
                        mol_type = other DNA
                        organism = synthetic construct
SEQUENCE: 10
ccgggatcat cgctctgcat c                                                     21

SEQ ID NO: 11           moltype = DNA   length = 20
FEATURE                 Location/Qualifiers
source                  1..20
                        mol_type = other DNA
                        organism = synthetic construct
SEQUENCE: 11
tcaatggcgg gtgctttaga                                                       20

SEQ ID NO: 12           moltype = DNA   length = 22
FEATURE                 Location/Qualifiers
source                  1..22
                        mol_type = other DNA
                        organism = synthetic construct
SEQUENCE: 12
tgctcactgc acaacatgaa ga                                                    22

SEQ ID NO: 13           moltype = DNA   length = 25
FEATURE                 Location/Qualifiers
source                  1..25
                        mol_type = other DNA
                        organism = synthetic construct
SEQUENCE: 13
ccacagagct attaaagtga cagtg                                                 25

SEQ ID NO: 14           moltype = DNA   length = 27
FEATURE                 Location/Qualifiers
source                  1..27
                        mol_type = other DNA
                        organism = synthetic construct
SEQUENCE: 14
aacaaactag gtttagagtc atcaagc                                               27

SEQ ID NO: 15           moltype = DNA   length = 20
FEATURE                 Location/Qualifiers
source                  1..20
                        mol_type = other DNA
                        organism = synthetic construct
SEQUENCE: 15
tcaacgttag cctcaccgtc                                                       20

SEQ ID NO: 16           moltype = DNA   length = 20
FEATURE                 Location/Qualifiers
source                  1..20
                        mol_type = other DNA
                        organism = synthetic construct
SEQUENCE: 16
cagggatcgt ctcattggca                                                       20

SEQ ID NO: 17           moltype = DNA   length = 20
FEATURE                 Location/Qualifiers
source                  1..20
                        mol_type = other DNA
```

-continued

```
                            organism = synthetic construct
SEQUENCE: 17
gaaaggctga ccgacgacta                                                              20

SEQ ID NO: 18               moltype = DNA   length = 20
FEATURE                     Location/Qualifiers
source                      1..20
                            mol_type = other DNA
                            organism = synthetic construct
SEQUENCE: 18
tgcgtggtac ttgggcataa                                                              20

SEQ ID NO: 19               moltype = DNA   length = 20
FEATURE                     Location/Qualifiers
source                      1..20
                            mol_type = other DNA
                            organism = synthetic construct
SEQUENCE: 19
gaagggacgg agtcagtgtg                                                              20

SEQ ID NO: 20               moltype = DNA   length = 20
FEATURE                     Location/Qualifiers
source                      1..20
                            mol_type = other DNA
                            organism = synthetic construct
SEQUENCE: 20
tgaatggtgc tgcactggat                                                              20

SEQ ID NO: 21               moltype = DNA   length = 20
FEATURE                     Location/Qualifiers
source                      1..20
                            mol_type = other DNA
                            organism = synthetic construct
SEQUENCE: 21
ctgagatcca cactcagccg                                                              20

SEQ ID NO: 22               moltype = DNA   length = 20
FEATURE                     Location/Qualifiers
source                      1..20
                            mol_type = other DNA
                            organism = synthetic construct
SEQUENCE: 22
gcatggtatc ggggaacact                                                              20

SEQ ID NO: 23               moltype = DNA   length = 20
FEATURE                     Location/Qualifiers
source                      1..20
                            mol_type = other DNA
                            organism = synthetic construct
SEQUENCE: 23
ataaagcgcg gatggcaaag                                                              20

SEQ ID NO: 24               moltype = DNA   length = 20
FEATURE                     Location/Qualifiers
source                      1..20
                            mol_type = other DNA
                            organism = synthetic construct
SEQUENCE: 24
ctcacccgaa gataggcgac                                                              20

SEQ ID NO: 25               moltype = DNA   length = 20
FEATURE                     Location/Qualifiers
source                      1..20
                            mol_type = other DNA
                            organism = synthetic construct
SEQUENCE: 25
acaagagtgc cgtgacaact                                                              20

SEQ ID NO: 26               moltype = DNA   length = 20
FEATURE                     Location/Qualifiers
source                      1..20
                            mol_type = other DNA
                            organism = synthetic construct
SEQUENCE: 26
agcttgattc caagggtccg                                                              20

SEQ ID NO: 27               moltype = DNA   length = 20
FEATURE                     Location/Qualifiers
source                      1..20
```

```
                        mol_type = other DNA
                        organism = synthetic construct
SEQUENCE: 27
cacggtccat catctctcgg                                                       20

SEQ ID NO: 28           moltype = DNA  length = 20
FEATURE                 Location/Qualifiers
source                  1..20
                        mol_type = other DNA
                        organism = synthetic construct
SEQUENCE: 28
catggagagg gagaggtcca                                                       20

SEQ ID NO: 29           moltype = DNA  length = 24
FEATURE                 Location/Qualifiers
source                  1..24
                        mol_type = other DNA
                        organism = synthetic construct
SEQUENCE: 29
aaccctaagg ccaacagtga aaag                                                  24

SEQ ID NO: 30           moltype = DNA  length = 21
FEATURE                 Location/Qualifiers
source                  1..21
                        mol_type = other DNA
                        organism = synthetic construct
SEQUENCE: 30
tcatgaggta gtctgtgagg t                                                     21

SEQ ID NO: 31           moltype = DNA  length = 20
FEATURE                 Location/Qualifiers
source                  1..20
                        mol_type = other DNA
                        organism = synthetic construct
SEQUENCE: 31
cagggccaac atgtcaggat                                                       20

SEQ ID NO: 32           moltype = DNA  length = 20
FEATURE                 Location/Qualifiers
source                  1..20
                        mol_type = other DNA
                        organism = synthetic construct
SEQUENCE: 32
tggcgacggc agttcttatt                                                       20
```